US010463133B2

(12) United States Patent
Sun et al.

(10) Patent No.: US 10,463,133 B2
(45) Date of Patent: Nov. 5, 2019

(54) PORTABLE SUNSCREEN APPLYING APPARATUS AND SUNSCREEN APPLICATION REMINDING METHOD

(71) Applicant: BOE TECHNOLOGY GROUP CO., LTD., Beijing (CN)

(72) Inventors: Junmin Sun, Beijing (CN); Tailiang Li, Beijing (CN); Guodong Huang, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 127 days.

(21) Appl. No.: 15/557,658

(22) PCT Filed: Feb. 22, 2017

(86) PCT No.: PCT/CN2017/074391
§ 371 (c)(1),
(2) Date: Sep. 12, 2017

(87) PCT Pub. No.: WO2018/018884
PCT Pub. Date: Feb. 1, 2018

(65) Prior Publication Data
US 2018/0289131 A1 Oct. 11, 2018

(30) Foreign Application Priority Data
Jul. 28, 2016 (CN) .......................... 2016 1 0608101

(51) Int. Cl.
*A45D 44/00* (2006.01)
*A45F 5/00* (2006.01)
*G01J 1/42* (2006.01)

(52) U.S. Cl.
CPC ................ *A45D 44/00* (2013.01); *A45F 5/00* (2013.01); *G01J 1/429* (2013.01);
(Continued)

(58) Field of Classification Search
CPC ......... A45F 5/00; A45D 44/00; A45D 44/005; G01J 1/429; G01J 1/50; G01J 1/42; A61B 5/6804; A61B 5/1112
See application file for complete search history.

(56) References Cited

U.S. PATENT DOCUMENTS 10,139,273 B2 * 11/2018 Poutiatine ............. G01J 1/4204
2003/0150998 A1 * 8/2003 Shin ........................ G01J 1/429
250/372

(Continued)

FOREIGN PATENT DOCUMENTS

CN 2775940 Y 4/2006
CN 102355514 A 2/2012
(Continued)

OTHER PUBLICATIONS

International Search Report of PCT/CN2017/074391 in Chinese, dated May 26, 2017 with English translation.
(Continued)

Primary Examiner — Hoi C Lau
(74) Attorney, Agent, or Firm — Collard & Roe, P.C.

(57) ABSTRACT

A portable sunscreen applying apparatus and a sunscreen application reminding method are provided, and the portable sunscreen applying apparatus includes: an ultraviolet processing device and a sunscreen accommodating device connected with the ultraviolet processing device, the sunscreen accommodating device is configured for accommodating sunscreens of different protection levels; the ultraviolet processing device includes: an ultraviolet detecting unit, for detecting current ultraviolet and obtaining an intensity of the current ultraviolet; and a sunscreen application reminding unit, for issuing a warning reminder of one of the sunscreens of the protection level corresponding to the intensity of the current ultraviolet. The ultraviolet processing device and the sunscreen accommodating device are provided together, the
(Continued)

intensity of the current ultraviolet is detected by the ultraviolet detecting unit in the ultraviolet processing device, and the user is reminded to use the appropriate sunscreen.

19 Claims, 4 Drawing Sheets

(52) U.S. Cl.
CPC .. *A45D 2044/007* (2013.01); *A45F 2005/008* (2013.01); *A45F 2200/0516* (2013.01); *G01J 2001/4266* (2013.01)

(56) References Cited

U.S. PATENT DOCUMENTS

| | | | |
|---|---|---|---|
| 2004/0155199 A1* | 8/2004 | Su | G01J 1/429 250/372 |
| 2005/0285050 A1* | 12/2005 | Bruce | G01J 1/429 250/474.1 |
| 2006/0204709 A1* | 9/2006 | Chen | G01J 1/50 428/68 |
| 2007/0041702 A1* | 2/2007 | Hwang | G01J 1/02 385/147 |
| 2008/0265170 A1* | 10/2008 | Ales | A61B 5/0059 250/372 |
| 2011/0288680 A1* | 11/2011 | Samain | A45D 44/005 700/239 |
| 2012/0153179 A1* | 6/2012 | Tew | B05B 11/3042 250/372 |
| 2012/0168333 A1* | 7/2012 | Mackay | A45D 34/00 206/459.1 |
| 2013/0300850 A1* | 11/2013 | Millikan | A61B 5/0077 348/77 |
| 2015/0041663 A1* | 2/2015 | Oliver | G01J 1/0219 250/372 |
| 2015/0083934 A1* | 3/2015 | Richter | G01J 1/50 250/473.1 |
| 2015/0102208 A1* | 4/2015 | Appelboom | G06F 19/3481 250/208.2 |
| 2016/0061657 A1* | 3/2016 | Lapiere | G01J 1/429 250/372 |
| 2016/0321395 A1* | 11/2016 | Colby | G06Q 30/0241 |
| 2017/0097258 A1* | 4/2017 | Albadawi | A61B 5/1112 |
| 2017/0144824 A1* | 5/2017 | Petrov | B65D 83/682 |
| 2017/0188948 A1* | 7/2017 | Chien | A61B 5/6804 |
| 2017/0249436 A1* | 8/2017 | Miller | G06F 19/326 |
| 2017/0350754 A1* | 12/2017 | Brown | G01J 1/429 |
| 2018/0017437 A1* | 1/2018 | Poutiatine | G01J 1/4204 |
| 2018/0120151 A1* | 5/2018 | Feldman | G01J 1/0219 |
| 2018/0289131 A1* | 10/2018 | Sun | A45F 5/00 |
| 2019/0049292 A1* | 2/2019 | Poutiatine | G01J 1/4204 |
| 2019/0060678 A1* | 2/2019 | Poutiatine | A61Q 17/04 |

FOREIGN PATENT DOCUMENTS

| | | |
|---|---|---|
| CN | 205849012 U | 1/2017 |
| JP | 2011-021906 A | 2/2011 |

OTHER PUBLICATIONS

Notice of Transmittal of the International Search Report of PCT/CN2017/074391 in Chinese, dated May 26, 2017.
Written Opinion of the International Searching Authority of PCT/CN2017/074391 in Chinese, dated May 27, 2017 with English translation of relevant parts.

* cited by examiner

//  PORTABLE SUNSCREEN APPLYING APPARATUS AND SUNSCREEN APPLICATION REMINDING METHOD

CROSS REFERENCE TO RELATED APPLICATIONS

This application is the National Stage of PCT/CN2017/074391 filed on Feb. 22, 2017, which claims priority under 35 U.S.C. § 119 of Chinese Application No. 201610608101.6 filed on Jul. 28, 2016, the disclosure of which is incorporated by reference.

TECHNICAL FIELD

Embodiments of the present disclosure relate to a portable sunscreen applying apparatus and a sunscreen application reminding method.

BACKGROUND

Ultraviolet whose wavelength is located between 0.32 microns to 0.40 microns is A ultraviolet. If human skin receives an excessive amount of radiation by the A ultraviolet, photo-condensation caused thereby will inhibit a normal function of a human immune system; ultraviolet whose wavelength is located between 0.28 microns to 0.32 microns is B ultraviolet, and in a case that the human skin receives the B ultraviolet radiation over a long period of time, which may result in skin cancer, cataract and immune system dysfunction and other hidden dangers. In daily life, people will inevitably be exposed to ultraviolet, a sunscreen should be used to protect the skin to prevent occurrence of the above-described diseases.

With respect to different intensities of ultraviolet, sunscreens of different protection levels should be used. Protection factors of the sunscreen mainly include preventive effect (PA) and sun protection factor (SPF), and PA is differentiated as PA+, PA++ and PA+++ whose protection effects are increased progressively; SPF refers to protection capability of a sun-proof skin-care product against ultraviolet; and the higher the SPF factor, the stronger the capability of protecting the skin.

If a device for detecting an ultraviolet intensity is separated from a container for containing skin-care products, a user may occasionally forget to carry the skin-care products, in this case, the user may be exposed to ultraviolet radiation for a long time, thereby his or her health will be affected adversely. In addition, with respect to different intensities of ultraviolet, skin-care products of different protection levels should be used, so it is necessary to monitor the ultraviolet intensity in real time, and to remind the user to use a skin-care product of a corresponding protection level in real time.

SUMMARY

At least one embodiment of the present disclosure provides a portable sunscreen applying apparatus, and the portable sunscreen applying apparatus comprises: an ultraviolet processing device and a sunscreen accommodating device connected with the ultraviolet processing device, wherein the sunscreen accommodating device is configured for accommodating sunscreens of different protection levels; the ultraviolet processing device comprises: a sunscreen accommodating device connected with the ultraviolet processing device, wherein the sunscreen accommodating device is configured for accommodating sunscreens of different protection levels; the ultraviolet processing device comprises: an ultraviolet detecting unit configured for detecting current ultraviolet and obtaining an intensity of the current ultraviolet; a sunscreen application reminding unit configured for issuing a warning reminder of using one of the sunscreens with the protection level corresponding to the intensity of the current ultraviolet.

For example, in the portable sunscreen applying apparatus provided by at least one embodiment of the present disclosure, the ultraviolet processing device further comprises a controller, and the controller is connected with the ultraviolet detecting unit and the sunscreen application reminding unit.

For example, in the portable sunscreen applying apparatus provided by at least one embodiment of the present disclosure, the ultraviolet processing device further comprises a communicating module, and the communicating module is connected with the controller.

For example, in the portable sunscreen applying apparatus provided by at least one embodiment of the present disclosure, the sunscreen accommodating device further comprises a driver, the driver is connected with the controller, and the driver is configured for driving the ejection of the sunscreens.

For example, in the portable sunscreen applying apparatus provided by at least one embodiment of the present disclosure, the ultraviolet processing device further comprises an ultraviolet level determining unit, and the ultraviolet level determining unit is configured for determining an intensity level of the current ultraviolet.

For example, in the portable sunscreen applying apparatus provided by at least one embodiment of the present disclosure, the ultraviolet level determining unit preliminarily divides an ultraviolet intensity into a first intensity range, a second intensity range, and a third intensity range, the ultraviolet intensity of the third intensity range is lager than the ultraviolet intensity of the second intensity range, the ultraviolet intensity of the second intensity range is lager than the ultraviolet intensity of the first intensity range, and the ultraviolet level determining unit outputs a light-level signal corresponding to the first intensity range, a moderate-level signal corresponding to the second intensity range, and a severe-level signal corresponding to the third intensity range.

For example, in the portable sunscreen applying apparatus provided by at least one embodiment of the present disclosure, the ultraviolet detecting unit is configured for obtaining the intensity of the current ultraviolet in an environment of the portable sunscreen applying apparatus according to a preset time period.

For example, the portable sunscreen applying apparatus provided by at least one embodiment of the present disclosure comprises a plurality of sunscreen accommodating devices, wherein the plurality of sunscreen accommodating devices are configured for accommodating the sunscreens of the different protection levels respectively.

For example, in the portable sunscreen applying apparatus provided by at least one embodiment of the present disclosure, the sunscreen application reminding unit stores an information of protection levels respectively corresponding to the sunscreens contained in the sunscreen accommodating device.

For example, in the portable sunscreen applying apparatus provided by at least one embodiment of the present disclosure, the sunscreen application reminding unit is a voice output unit, an image display unit or a vibration unit.

For example, the portable sunscreen applying apparatus provided by at least one embodiment of the present disclosure further comprises a wristband suitable for being worn on a wrist of a user, wherein the ultraviolet processing device is connected with the sunscreen accommodating device through the wristband.

For example, in the portable sunscreen applying apparatus provided by at least one embodiment of the present disclosure, the wristband is provided with an accommodation space, and the sunscreen accommodating device is arranged in the accommodation space.

For example, in the portable sunscreen applying apparatus provided by at least one embodiment of the present disclosure, the wristband is provided with a fastener, and the fastener is configured for adjusting a limiting space of the wristband.

For example, in the portable sunscreen applying apparatus provided by at least one embodiment of the present disclosure, the ultraviolet processing device has an outer wall, the outer wall is provided with an accommodation space, and the sunscreen accommodating device is in the accommodation space.

For example, in the portable sunscreen applying apparatus provided by at least one embodiment of the present disclosure, a size of the accommodation space is adjustable to adapt to different sizes of the sunscreen accommodating device.

At least one embodiment of the present disclosure further provides a sunscreen application reminding method, and the method comprises: obtaining the intensity of the current ultraviolet with the portable sunscreen applying apparatus described above, and issuing the warning reminder of using the sunscreen with the protection level corresponding to the intensity of the current ultraviolet.

For example, the sunscreen application reminding method provided by at least one embodiment of the present disclosure further comprises: dividing an ultraviolet intensity into a first intensity range, a second intensity range, and a third intensity range, wherein the ultraviolet intensity of the third intensity range is lager than the ultraviolet intensity of the second intensity range, the ultraviolet intensity of the second intensity range is lager than the ultraviolet intensity of the first intensity range; and outputting a light-level signal corresponding to the first intensity range, outputting a moderate-level signal corresponding to the second intensity range, or outputting a severe-level signal corresponding to the third intensity range.

For example, in the sunscreen application reminding method provided by at least one embodiment of the present disclosure, modes of the warning reminder comprise: voice output, image display or vibration.

For example, in the sunscreen application reminding method provided by at least one embodiment of the present disclosure, in a case that the mode of the warning reminder is voice output, a preset voice signal is output; in a case that the mode of the warning reminder is image display, a preset image signal is output; and in a case that the mode of the warning reminder is vibration, a vibration signal of a preset frequency is output.

BRIEF DESCRIPTION OF THE DRAWINGS

In order to clearly illustrate the technical solution of the embodiments of the present disclosure, the drawings of the embodiments will be briefly described in the following. It is obvious that the described drawings are only related to some embodiments of the present disclosure, and those skilled in the art can also obtain other drawings without any inventive work according to the drawings, and thus are not limitative of the present disclosure.

DETAILED DESCRIPTION

In order to make objects, technical details and advantages of the embodiments of the present disclosure apparent, the technical solutions of the embodiments will be described in a clearly and fully understandable way in connection with the drawings related to the embodiments of the disclosure. It is obvious that the described embodiments are just a part but not all of the embodiments of the disclosure. Based on the described embodiments herein, those skilled in the art can obtain other embodiment(s), without any inventive work, which should be within the scope of the disclosure.

Unless otherwise defined, the technical terms or scientific terms used herein have the same meanings as commonly understood by one of ordinary skill in the art to which the present invention belongs. The terms "first," "second," etc., which are used in the description and the claims of the present application for invention, are not intended to indicate any sequence, amount or importance, but distinguish various components. The terms "comprises," "comprising," "includes," "including," etc., are intended to specify that the elements or the objects stated before these terms encompass the elements or the objects and equivalents thereof listed after these terms, but do not preclude the other elements or objects. The phrases "connect", "connected", etc., are not intended to define a physical connection or mechanical connection, but may include an electrical connection, directly or indirectly. "Over," "under," "right," "left" and the like are only used to indicate relative position relationship, and when the position of the object which is described is changed, the relative position relationship may be changed accordingly.

At least one embodiment of the present disclosure provides a portable sunscreen applying apparatus and a sunscreen application reminding method. In at least one embodiment of the present disclosure, an intensity of current ultraviolet is detected by an ultraviolet detecting unit of the portable sunscreen applying apparatus, and the intensity of the current ultraviolet is feed back to a sunscreen application reminding unit, reminding a user to use a sunscreen of a corresponding protection level according to the intensity of the current ultraviolet, thus, the user can obtain a timely, accurate and effective ultraviolet protection to reduce or eliminate hidden dangers caused by ultraviolet radiation to the user, and to improve quality of life.

Figure 1A:
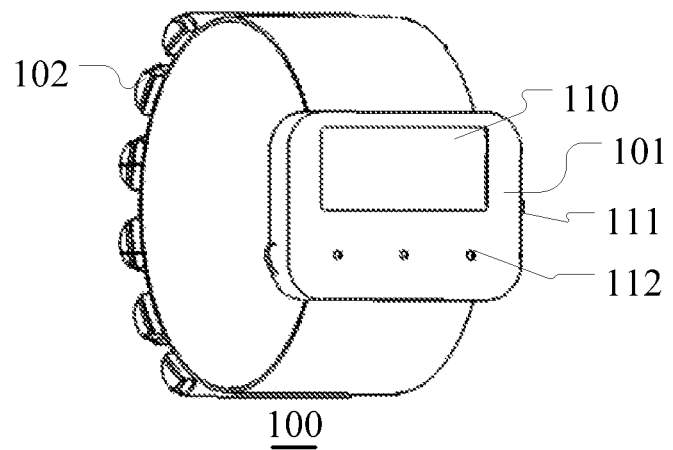
FIG. 1A is a schematic diagram of a structure of a portable sunscreen applying apparatus provided by an embodiment of the present disclosure.

At least one embodiment of the present disclosure provides a portable sunscreen applying apparatus, and FIG. 1A is a schematic diagram of a structure of a portable sunscreen applying apparatus provided by an embodiment of the present disclosure. As illustrated in FIG. 1A, the portable sunscreen applying apparatus 100 comprises: an ultraviolet processing device 101 and a sunscreen accommodating device 102 connected with the ultraviolet processing device 101, the sunscreen accommodating device is configured for accommodating sunscreens of different protection levels, and the ultraviolet processing device 101 comprises: an ultraviolet detecting unit and a sunscreen application reminding unit, the ultraviolet detecting unit is configured for detecting ultraviolet and obtaining an intensity of the current ultraviolet; the sunscreen application reminding unit is configured for issuing a warning reminder of using one of the sunscreens with the protection level corresponding to the intensity of the current ultraviolet.

For example, in the portable sunscreen applying apparatus 100, the ultraviolet processing device 101 and the sunscreen accommodating device 102 are connected together, for example, the two may be integrally formed or fixed to each other, and the intensity of the current ultraviolet is detected by the ultraviolet detecting unit in the ultraviolet processing device 101, so it is convenient to remind the user of which protection level of sunscreen to use, or instruct the user of a sunscreen in which sunscreen accommodating device 102 to use directly. Besides, the portable sunscreen applying apparatus 100 according to the embodiment for example holds a plurality of sunscreens corresponding to different ultraviolet protection levels conveniently, and at the same time, it is also easy for the user to find the sunscreen corresponding to the intensity of the current ultraviolet immediately.

For example, the sunscreen accommodating device 102 is detachable from the ultraviolet processing device 101, so as to fill or replace the sunscreen.

Figure 1B:
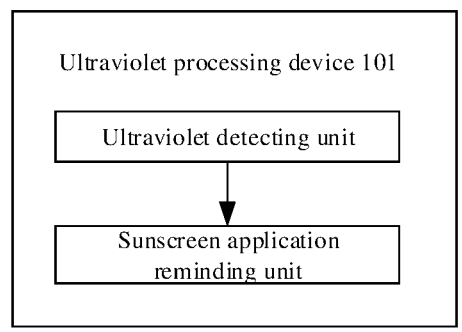
FIG. 1B to FIG. 1D are schematic diagrams of examples of an ultraviolet processing device.

For example, FIG. 1B is a schematic diagram of an example of the ultraviolet processing device, and the ultraviolet processing device 101 comprises the ultraviolet detecting unit and the sunscreen application reminding unit, the ultraviolet detecting unit provides a detection result to the sunscreen application reminding unit, and the sunscreen application reminding unit issues the warning reminder according to the result. For example, the ultraviolet detecting unit is an ultraviolet sensor, and the ultraviolet sensor, for example, comprises a semiconductor photosensitive element and a signal detecting circuit. For example, the semiconductor photosensitive element is a silicon-based or GaN-based ultraviolet sensor. For example, the signal detecting circuit comprises a switching transistor, a capacitor, an amplifier and the like. The sunscreen application reminding unit may have different structures and components according to different reminding modes, specifically as described below.

Figure 1C:
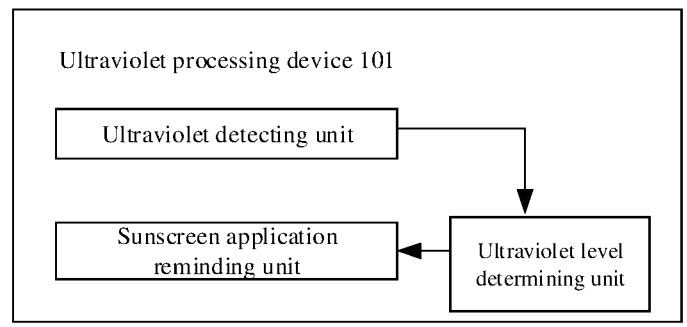

FIG. 1C is a schematic diagram of another example of the ultraviolet processing device, for example, the ultraviolet processing device 101 further comprises an ultraviolet level determining unit, and the ultraviolet level determining unit is configured for determining an intensity level of the current ultraviolet. The ultraviolet level determining unit may be an analog-digital converter circuit (AD circuit), to convert an analog signal into a digital signal, and the digital signal may be provided to the sunscreen application reminding unit. The ultraviolet level determining unit may also be implemented by a dedicated processing device or a general processing device, and thus it further has a certain calculation function and a certain judgment function.

For example, an ultraviolet index comprises 0 to 15 levels, and the larger the level the stronger the ultraviolet intensity indicated thereby. The ultraviolet level determining unit 107 preliminarily divides an ultraviolet intensity into a first intensity range, a second intensity range, and a third intensity range, the ultraviolet intensity of the third intensity range is lager than the ultraviolet intensity of the second intensity range, the ultraviolet intensity of the second intensity range is lager than the ultraviolet intensity of the first intensity range, and the ultraviolet level determining unit 107 outputs a light-level signal corresponding to the first intensity range, a moderate-level signal corresponding to the second intensity range, and a severe-level signal corresponding to the third intensity range.

For example, 0 to 2 levels are weakest levels, and the levels of ultraviolet are security levels, with respect to which no protection measure needs to be taken; 3 to 6 levels are middle levels, and the levels of ultraviolet are set to the first intensity range, with respect to which a sunscreen with a sun protection factor (SPF) no less than 20 may be embrocated; 7 to 9 levels are stronger levels, and the levels of ultraviolet are set to the second intensity range, with respect to which a sunscreen with a SPF no less than 30 and a preventive effect (PA) of PA++ above may be embrocated; ultraviolet indexes greater than 10 are strongest levels, and the levels of ultraviolet are set to the third intensity range, and in a case that the ultraviolet is within the intensity range, one should try not to go out, but in a case that one has to, he or she should apply a sunscreen with a SPF greater than 50, and a PA of PA+++ above.

Herein, the SPF refers to protection capability of a sun-proof skin-care product against ultraviolet. The higher the SPF index, the greater the capability of protecting the skin. Different SPFs indicate different effective sun-proof time periods. For example, SPF 20=20*10=200 minutes; SPF 30=30*10=300 minutes; SPF 50=50*10=500 minutes.

For example, the ultraviolet detecting unit is configured for obtaining an intensity of the current ultraviolet in the portable sunscreen applying apparatus according to a preset time period. The preset time period may be a fixed time period, for example, 5 minutes, 10 minutes, 20 minutes or 30 minutes; or the preset time period may be shortened as the increase of the intensity of the current ultraviolet; in a case that it is detected that the intensity of the current ultraviolet is within the first intensity range, the preset time period is 30 minutes; in a case that it is detected that the intensity of the current ultraviolet is within the second intensity range, the preset time period is 15 minutes; and in a case that it is detected that the intensity of the current ultraviolet is within the third intensity range, the preset time period is 5 minutes.

Figure 1D:
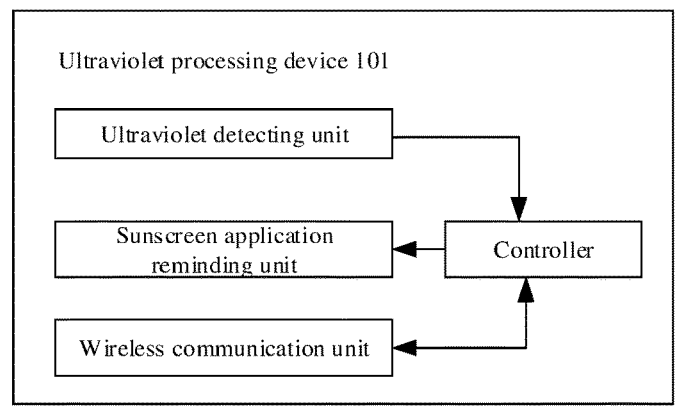

FIG. 1D is schematic diagrams of another example of the ultraviolet processing device, and as compared with that in FIG. 1B, the ultraviolet processing device further comprises a controller. The controller is connected with the ultraviolet detecting unit and the sunscreen application reminding unit; the controller obtains the detection result of the intensity of the current ultraviolet from the ultraviolet detecting unit, and controls the sunscreen application reminding unit to implement a corresponding reminding operation according to the detection result. Moreover, the controller may also be used as the ultraviolet level determining unit. The controller may be implemented, for example, by a dedicated or general purpose computing device, e.g., a digital signal processor (DSP), a microcontroller, a central processing unit (CPU) and the like.

As illustrated in FIG. 1A, the ultraviolet processing device 101 may further be provided with a display screen 110, as an example in which the sunscreen application reminding unit is an image display device. In a case that a sunscreen application reminding mode is an image reminder or a text reminder, the display screen 110 is configured for outputting an image information or a text information. The user selects the sunscreen of the corresponding protection level according to the image information or the text information. The display screen 110 may be a liquid crystal display panel, an organic light-emitting diode (OLED) display panel, or an electronic ink display panel.

As illustrated in FIG. 1A, the ultraviolet processing device 101 may further be provided with a first button 111 functioning as a timing switch. Each of the sunscreens has a corresponding effective sun-proof time period, the user may set a time period after spraying the sunscreen, so as to remind the user when the effective sun-proof time period of the sunscreen comes to an end.

Figure 2:
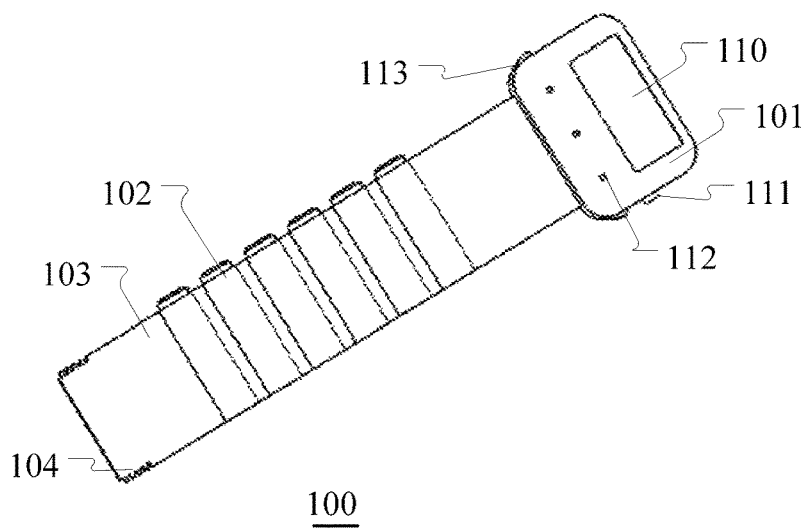
FIG. 2 is a schematic diagram of a structure of the portable sunscreen applying apparatus in FIG. 1A after unfolding.

For example, FIG. 2 is a schematic diagram of a structure of the portable sunscreen applying apparatus in FIG. 1A after unfolding; as illustrated in FIG. 2, the portable sunscreen applying apparatus 100 comprises six sunscreen accommodating devices 102, the six sunscreen accommodating devices 102 accommodating sunscreens corresponding to three protection levels. The embodiment of the present disclosure is not limited to the specific number of the sunscreen accommodating devices 102.

For example, as illustrated in FIG. 2, in the six sunscreen accommodating devices 102, only two sunscreen accommodating devices 102 closest to the ultraviolet processing device 101 contain the sunscreen with a SPF no less than 20, to prevent ultraviolet within the first intensity range, two middle sunscreen accommodating devices 102 contain the sunscreen with a SPF no less than 30, to prevent ultraviolet within the second intensity range, and two sunscreen accommodating devices 102 far away from the ultraviolet processing device 101 contain the sunscreen with a SPF no less than 50, to prevent ultraviolet within the third intensity range.

For example, as illustrated in FIG. 2, the portable sunscreen applying apparatus 100 comprises a sensor 112, and as an example of the ultraviolet detecting unit, ultraviolet in the current environment is sensed by the sensor.

For example, as illustrated in FIG. 2, the portable sunscreen applying apparatus 100 further comprises a wristband 103 adapted to be worn on a wrist of the user, and the ultraviolet processing device 101 and the sunscreen accommodating device 102 are connected with each other through the wristband 103. The wristband 103 is flexible and bendable. The wristband 103 may be provided with a fastener 104, which may adjust a length of the wristband 103 by opening a second button 113; in a case that the length of the wristband 103 is adjusted to a suitable size, restriction space of the wristband 103 is fixed by the fastener 104, to meet needs of different users.

For example, as illustrated in FIG. 2, the wristband 103 is provided with a plurality of accommodation spaces, and each of the accommodation spaces has a sunscreen accommodating device 102 placed therein. The accommodation space is defined by a material having a certain flexibility which is provided oppositely and protruding from the wristband 103.

For example, the sunscreen application reminding unit stores an information of protection levels respectively corresponding to the sunscreens contained in the sunscreen accommodating device 102.

For example, the modes of the warning of the sunscreen application reminding unit comprise voice output, image display or vibration. If the mode of the sunscreen application reminding unit is voice output, it is a voice output unit, e.g., a speaker, to output a preset voice signal, to perform voice broadcast, so as to remind the user; if the mode of the sunscreen application reminding unit is image display, it is an image display unit, e.g., a display screen, to output a preset image signal and feed back onto the display screen, so as to remind the user; and if the mode of the sunscreen application reminding unit is vibration, it is a vibration unit, e.g., a piezoelectric motor, to output a vibration signal of a preset frequency, so as to remind the user.

As illustrated in FIG. 1D, for example, the ultraviolet processing device 101 may further comprise a communicating module, for example, the communicating module is a wireless communicating module, the wireless communicating module is connected with the controller, and the wireless communicating module, for example, is connected with a mobile terminal, e.g., a smartphone or a smart watch, etc., for example, in a transmission mode of low power consumption, e.g., through Bluetooth or ZigBee or a wireless local area network (WIFI); for example, the user may view the ultraviolet intensity and the remainder of the sunscreen through an application (APP) installed on a mobile phone or a watch, or the portable sunscreen applying apparatus will transfer the reminding information to the APP installed on the mobile phone to remind the user to apply the sunscreen of the corresponding protection level.

For example, the wireless communicating module in the ultraviolet processing device 101 may be replaced by a wired communicating module, the wired communicating module is connected with the controller, and the wired communicating module may be, for example, a connecting line provided in the ultraviolet processing device 101.

For example, the sunscreen application reminding unit may have an information about contents of the sunscreens contained in the respective sunscreen accommodating devices stored therein, and remind the user to timely replace the sunscreen by voice broadcast or image or text output.

For example, hardware implementing the above-described storage functions comprises: a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. Such a propagated signal may take any of a variety of forms, including, but not limited to, electro-magnetic, optical, or any suitable combination thereof.

Figure 3:
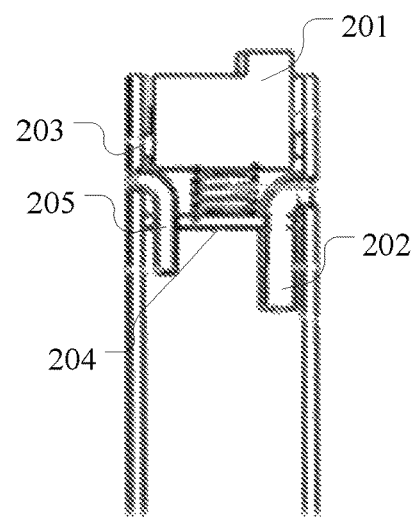
FIG. 3 is a schematic diagram of a structure of a sunscreen accommodating device.

FIG. 3 is an internal structural schematic diagram of an example of the sunscreen accommodating device 102; and for example, the sunscreen accommodating device 102 comprises a pressing head 201, an outlet check valve 202, a sealing rubber pad 203, a barrier plate 204, and an inlet check valve 205. A process of extruding the sunscreen with the sunscreen accommodating device 10 is that: the user presses the pressing head 201 of the corresponding sunscreen accommodating device according to the reminding information, or a controller is provided in the ultraviolet processing device, the sunscreen accommodating device is provided therein with a driver, the driver is used for driving the sunscreen to be spouted, a connecting line is provided on the wristband 103, the driver and the controller are connected through the connecting line, the connecting line transmits a signal issued by the controller to the driver, the driver receives the signal to perform subsequent work, for example, according to a corresponding reminding signal, the controller controls the driver to drive the pressing head 201 to move downward, to squeeze the sealing rubber pad 203, allowing the outside air to enter the inlet check valve 205, the air compresses the sunscreen below the barrier plate 204, allowing the sunscreen to pass through the outlet check valve 202, and finally the sunscreen is extruded from the outlet.

Figure 4:
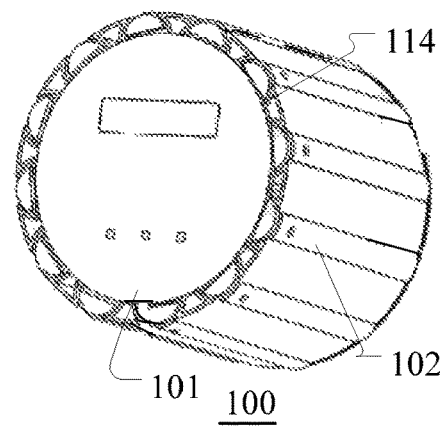
FIG. 4 is a schematic diagram of a structure of a portable sunscreen applying apparatus provided by another embodiment of the present disclosure.

At least one embodiment of the present disclosure further provides a portable sunscreen applying apparatus, FIG. 4 is a schematic diagram of a structure of a portable sunscreen applying apparatus provided by the embodiment of the present disclosure, and the portable sunscreen applying apparatus 100 comprises: an ultraviolet processing device 101 and a sunscreen accommodating device 102 connected with the ultraviolet processing device 101, and the ultraviolet processing device 101 comprises: an ultraviolet detecting unit and a sunscreen application reminding unit, the ultraviolet detecting unit is configured for detecting ultraviolet and obtaining an intensity of a current ultraviolet; the sunscreen application reminding unit is configured for issuing a warning reminder of a sunscreen of a protection level corresponding to the intensity of the current ultraviolet; and the sunscreen accommodating device is configured for accommodating sunscreens of different protection levels. The ultraviolet processing device 101 may likewise be an example as illustrated in FIG. 1B to FIG. 1D.

For example, as illustrated in FIG. 4, the ultraviolet processing device 101 has an outer wall 114, the outer wall 114 is provided with a plurality of accommodation spaces 117, and the sunscreen accommodating devices 102 are arranged in the accommodation spaces respectively.

Figure 5:
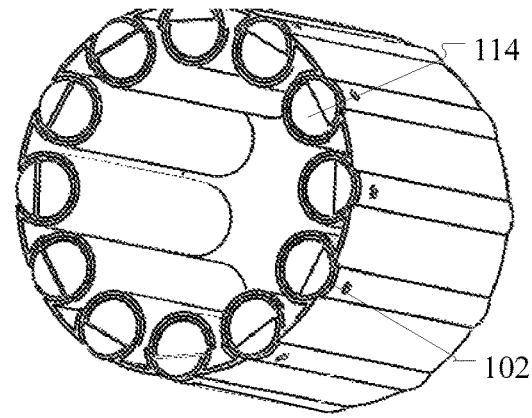
FIG. 5 is a schematic diagram of a structure of a combination of an outer wall and the sunscreen accommodating device of the portable sunscreen applying apparatus in FIG. 4.
Figure 6:
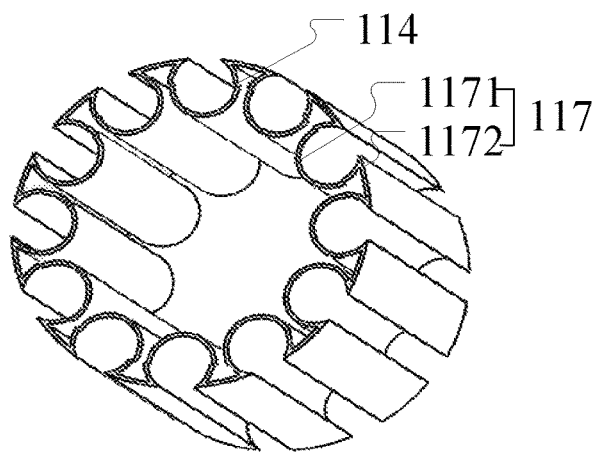
FIG. 6 is a schematic diagram of a structure of the outer wall of the portable sunscreen applying apparatus in FIG. 4.

For example, FIG. 5 is a schematic diagram of a structure of a combination of an outer wall and the sunscreen accommodating device of the portable sunscreen applying apparatus in FIG. 4, FIG. 6 is a schematic diagram of a structure of the outer wall of the portable sunscreen applying apparatus in FIG. 4; the outer wall 114 has a shape including an annular shape and a polygonal shape, the accommodation space 117 includes a concave portion and a clamping portion, the accommodation space is defined by a recess structure 1171 and an arc piece 1172 provided on the outer wall, and respective sunscreen accommodating devices 102 are placed in respective accommodation spaces.

It should be noted that, the plurality of accommodation spaces may be set to different sizes, to accommodate different sunscreen accommodating devices. In addition, the size of the accommodation space may also be adjusted by flexibility of the material, to be adapted to different sizes of sunscreen accommodating devices.

Figure 7:
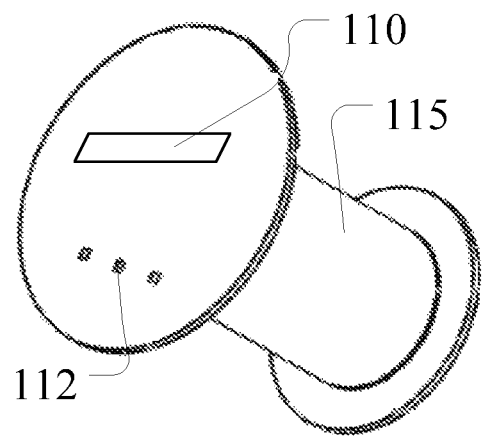
FIG. 7 is a schematic diagram of a structure of an internal structural of the portable sunscreen applying apparatus in FIG. 4.

For example, FIG. 7 is a schematic diagram of a structure of an internal structural of the portable sunscreen applying apparatus in FIG. 4; a battery 115 may be provided in a cylinder, and wires may also be provided in the cylinder. Battery electrodes are provided at both ends of the battery 115, and a sensor 112 and a display screen 110 are provided on one of the battery electrode at one end; a shape of the battery 115 is not limited herein, which may be any suitable shapes.

Figure 8:
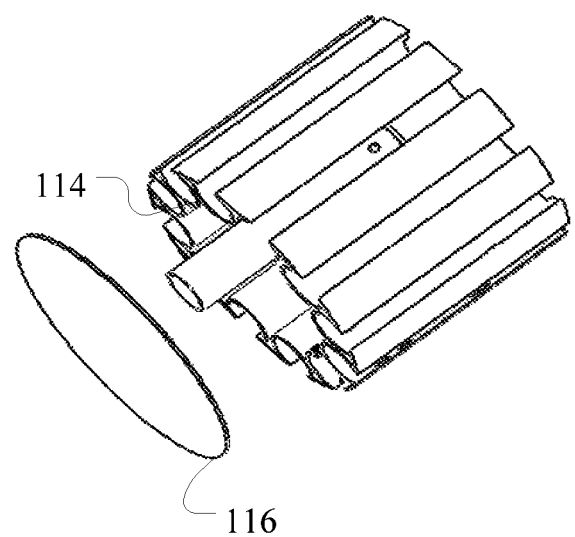
FIG. 8 is a schematic diagram illustrating a process of replacing the sunscreen of the portable sunscreen applying apparatus in FIG. 4.

FIG. 8 is a schematic diagram illustrating a process of replacing the sunscreen of the portable sunscreen applying apparatus in FIG. 4, the ultraviolet processing device further comprises a baseplate 116, the baseplate 116 is provided with a plurality of recesses, an end of the sunscreen accommodating device away from the sunscreen outlet is defined in the recesses, and the baseplate 116 is fixed to a lower electrode plate by a nut. A process of replacing the sunscreen is: removing the baseplate 116, removing the sunscreen accommodating device, placing a new sunscreen in the sunscreen accommodating device, or directly replacing with a new sunscreen accommodating device containing a sunscreen.

For example, the process of the portable sunscreen applying apparatus replacing the sunscreen may be automatically controlled. For example, in a case of wired controlling, in the process of replacing the sunscreen, as illustrated in FIG. 7, it may be automatically ejected by an ejection mechanism provided between the baseplate 116 and the accommodation space as driven by the wiring provided in the cylinder, so that the baseplate 116 is separated from the accommodation space, to further perform the subsequent process of replacing the sunscreen accommodating device; or, in a case of wireless controlling, no wiring is needed inside the cylinder in FIG. 7, a signal is transmitted by a wireless apparatus to a signal receiving unit on the baseplate 116 or the outer wall 114, to drive the ejection mechanism provided between the baseplate 116 and the accommodation space to automatically eject, so as to cause the baseplate 116 to be separated from the accommodation space.

The internal structural schematic diagram of the sunscreen accommodating device 102, can refer to the above-described relevant contents, which will not be repeated herein.

At least one embodiment of the present disclosure further provides a sunscreen application reminding method, and the method comprises: obtaining the intensity of the current ultraviolet with any one of the above-described portable sunscreen applying apparatuses, obtaining a warning reminder of using the sunscreen with the protection level corresponding to the intensity of the current ultraviolet.

The portable sunscreen applying apparatus comprises an ultraviolet processing device and a sunscreen accommodating device connected with the ultraviolet processing device, the ultraviolet processing device and the sunscreen accommodating device are provided together, and both of which are used in coordination with each other. The ultraviolet processing device comprises: an ultraviolet detecting unit and a sunscreen application reminding unit, the ultraviolet detecting unit is configured for detecting ultraviolet and obtaining the intensity of the current ultraviolet; the sunscreen application reminding unit is configured for issuing the warning reminder of the sunscreen of the protection level corresponding to the intensity of the current ultraviolet; and the sunscreen accommodating device is configured for accommodating sunscreens of different protection levels. The ultraviolet processing device 101 may likewise be any one of the examples as illustrated in FIG. 1B to FIG. 1D.

The ultraviolet processing device comprises an ultraviolet level determining unit, and the ultraviolet level determining unit preliminarily divides the ultraviolet intensity into a first intensity range, a second intensity range, and a third intensity range, the ultraviolet intensity of the third intensity range is lager than the ultraviolet intensity of the second intensity range, the ultraviolet intensity of the second intensity range is lager than the ultraviolet intensity of the first intensity range, and the ultraviolet level determining unit outputs a light-level signal corresponding to the first intensity range, a moderate-level signal corresponding to the second intensity range, and a severe-level signal corresponding to the third intensity range.

For example, an ultraviolet index includes 0 to 15 base levels; and the larger the level, the stronger the ultraviolet intensity indicated thereby. In a case that the ultraviolet indexes are 0 to 2, they are set to weakest levels, and the levels of ultraviolet are security levels, with respect to which no protection measure needs to be taken; 3 to 6 levels are middle levels, and the levels of ultraviolet are set to the first intensity range, with respect to which a sunscreen with a sun protection factor (SPF) no less than 20 may be embrocated; 7 to 9 levels are stronger levels, and the levels of ultraviolet are set to the second intensity range, with respect to which a sunscreen with a SPF no less than 30 and a preventive effect (PA) of PA++ above may be embrocated; ultraviolet factors greater than 10 are strongest levels, and the levels of ultraviolet are set to the third intensity range, and in a case that ultraviolet is within the intensity range, one should try not to go out, but when one has to, he or she should apply a sunscreen with a SPF greater than 50, and a PA of PA+++ above.

Herein, the SPF refers to protection capability of a sun-proof skin-care product against ultraviolet. The higher the SPF factor, the greater the capability of protecting the skin. Different SPFs indicate different effective sun-proof time periods. For example, SPF 20=20*10=200 minutes; SPF 30=30*10=300 minutes; SPF 50=50*10=500 minutes.

For example, the ultraviolet detecting unit is configured for obtaining the current ultraviolet intensity in the portable sunscreen applying apparatus according to a preset time period. The preset time period may be a fixed time period, for example, 5 minutes, 10 minutes, 20 minutes or 30 minutes; or the preset time period may be shortened as the current ultraviolet intensity gradually increases; in a case that it is detected that the intensity of the current ultraviolet is within the first intensity range, the preset time period is 30 minutes; in a case that it is detected that the intensity of the current ultraviolet is within the second intensity range, the preset time period is 15 minutes; and in a case that it is detected that the intensity of the current ultraviolet is within the third intensity range, the preset time period is 5 minutes.

For example, the sunscreen application reminding method comprises voice output, image display and vibration. For example, if the reminding method is voice output, a preset voice signal is output, to perform voice broadcast directly, so as to remind the user of which protection level of a sunscreen to apply, or a controller receives a voice reminding signal, and a driver directly drive a pressing head 201 to move downward, to squeeze the sunscreen; if the reminding method is image display, a preset image signal is output, so as to remind the user of which protection level of a sunscreen to apply, directly in a mode of an image or a text; and if the reminding method is vibration, a vibration signal of a preset frequency is output.

The portable sunscreen applying apparatuses provided by the embodiments of the present disclosure have at least one of advantageous effects as follows:

(1) the ultraviolet processing device and the sunscreen accommodating device are provided together, the intensity of the current ultraviolet may be detected by the ultraviolet processing device, which may remind the user, and instruct the user to apply the appropriate sunscreen; and (2) with respect to different ultraviolet intensities, the sunscreen of the corresponding protection level are automatically spouted, to provide protection to the user.

There are some points to be illustrated:

(1) Drawings of the embodiments of the present disclosure only refer to structures related with the embodiments of the present disclosure, and other structures may refer to general design.

(2) In order to make it clear, in the drawings for illustrating the embodiment of the present disclosure, a thickness of a layer or a region is magnified or reduced, that is, those drawings are not drawn according to actual proportion. It should be understood that, when elements such as a layer, a film, a region or a substrate and the like are called to be "above" or "below" another element, the element may be directly located "on" or "beneath" the other element, or there may be an intermediate element.

(3) In case of no conflict, the embodiments of the present disclosure and the features of the embodiments may be combined with each other to form new embodiments.

What are described above is related to the illustrative embodiments of the disclosure only and not limitative to the scope of the disclosure; the scopes of the disclosure are defined by the accompanying claims.

The present application claims priority of Chinese Patent Application No. 201610608101.6 filed on Jul. 28, 2016, the present disclosure of which is incorporated herein by reference in its entirety as part of the present application.

What is claimed is:

1. A portable sunscreen applying apparatus, comprising: an ultraviolet processing device and a sunscreen accommodating device connected with the ultraviolet processing device,
    wherein the sunscreen accommodating device is configured for accommodating sunscreens of different protection levels;
    the ultraviolet processing device comprises:
    an ultraviolet detecting unit configured for detecting current ultraviolet and obtaining an intensity of the current ultraviolet;
    a sunscreen application reminding unit configured for issuing a warning reminder of using one of the sunscreens with the protection level corresponding to the intensity of the current ultraviolet;
    the ultraviolet processing device is further provided with a first button functioning as a timing switch, and the first button is configured for reminding when the effective sun-proof time period of the sunscreen comes to an end;
    the ultraviolet processing device further comprises a baseplate, the baseplate is provided with a plurality of recesses, an end of the sunscreen accommodating device away from the sunscreen outlet is defined in one of the recesses; and
    the sunscreen accommodating device comprises a pressing head, an outlet check valve, a sealing rubber pad, a barrier plate, and an inlet check valve.

2. The portable sunscreen applying apparatus according to claim 1, wherein the ultraviolet processing device further comprises a controller, and the controller is connected with the ultraviolet detecting unit and the sunscreen application reminding unit.

3. The portable sunscreen applying apparatus according to claim 2, wherein the ultraviolet processing device further comprises a communicating module, and the communicating module is connected with the controller.

4. The portable sunscreen applying apparatus according to claim 2, wherein the sunscreen accommodating device further comprises a driver, the driver is connected with the controller, and the driver is configured for driving the ejection of the sunscreens.

5. The portable sunscreen applying apparatus according to claim 1, wherein the ultraviolet processing device further comprises an ultraviolet level determining unit, and the ultraviolet level determining unit is configured for determining an intensity level of the current ultraviolet.

6. The portable sunscreen applying apparatus according to claim 5, wherein the ultraviolet level determining unit preliminarily divides an ultraviolet intensity into a first intensity range, a second intensity range, and a third intensity range, the ultraviolet intensity of the third intensity range is lager than the ultraviolet intensity of the second intensity range, the ultraviolet intensity of the second intensity range is lager than the ultraviolet intensity of the first intensity range, and the ultraviolet level determining unit outputs a light-level signal corresponding to the first intensity range, a moderate-level signal corresponding to the second intensity range, and a severe-level signal corresponding to the third intensity range.

7. The portable sunscreen applying apparatus according to claim 1, wherein the ultraviolet detecting unit is configured for obtaining the intensity of the current ultraviolet in an environment of the portable sunscreen applying apparatus according to a preset time period.

8. The portable sunscreen applying apparatus according to claim 1, comprising a plurality of sunscreen accommodating devices, wherein the plurality of sunscreen accommodating devices are configured for accommodating the sunscreens of the different protection levels respectively.

9. The portable sunscreen applying apparatus according to claim 8, wherein the sunscreen application reminding unit stores an information of protection levels respectively corresponding to the sunscreens contained in the sunscreen accommodating device.

10. The portable sunscreen applying apparatus according to claim 1, wherein the sunscreen application reminding unit is a voice output unit, an image display unit or a vibration unit.

11. The portable sunscreen applying apparatus according to claim 1, further comprising a wristband suitable for being worn on a wrist of a user, wherein the ultraviolet processing device is connected with the sunscreen accommodating device through the wristband.

12. The portable sunscreen applying apparatus according to claim 11, wherein the wristband is provided with an accommodation space, and the sunscreen accommodating device is arranged in the accommodation space.

13. The portable sunscreen applying apparatus according to claim 11, wherein the wristband is provided with a fastener, and the fastener is configured for adjusting a limiting space of the wristband.

14. The portable sunscreen applying apparatus according to claim 1, wherein the ultraviolet processing device has an outer wall, the outer wall is provided with an accommodation space, and the sunscreen accommodating device is in the accommodation space.

15. The portable sunscreen applying apparatus according to claim 14, wherein a size of the accommodation space is adjustable to adapt to different sizes of the sunscreen accommodating device.

16. A sunscreen application reminding method, comprising:
providing the portable sunscreen applying apparatus according to claim 1;
obtaining the intensity of the current ultraviolet by the ultraviolet detecting unit in the portable sunscreen applying apparatus, and
issuing the warning reminder of using the sunscreen with the protection level corresponding to the intensity of the current ultraviolet by the sunscreen application reminding unit in the portable sunscreen applying apparatus.

17. The sunscreen application reminding method according to claim 16, further comprising:
dividing an ultraviolet intensity into a first intensity range, a second intensity range, and a third intensity range, wherein the ultraviolet intensity of the third intensity range is lager than the ultraviolet intensity of the second intensity range, the ultraviolet intensity of the second intensity range is lager than the ultraviolet intensity of the first intensity range; and
outputting a light-level signal corresponding to the first intensity range, outputting a moderate-level signal corresponding to the second intensity range, or outputting a severe-level signal corresponding to the third intensity range.

18. The sunscreen application reminding method according to claim 16, wherein modes of the warning reminder comprise: voice output, image display or vibration.

19. The sunscreen application reminding method according to claim 18, wherein in a case that the mode of the warning reminder is voice output, a preset voice signal is output; in a case that the mode of the warning reminder is image display, a preset image signal is output; and in a case that the mode of the warning reminder is vibration, a vibration signal of a preset frequency is output.

* * * * *